(12) United States Patent
Yakovenko

(10) Patent No.: US 6,357,719 B1
(45) Date of Patent: Mar. 19, 2002

(54) MICROTOOL MOUNT

(76) Inventor: Sergey A. Yakovenko, Kolomenskiy Proezd 8-3-299, Moscow 115446 (RU)

( * ) Notice: Subject to any disclaimer, the term of this patent is extended or adjusted under 35 U.S.C. 154(b) by 0 days.

(21) Appl. No.: 09/596,409

(22) Filed: Jun. 19, 2000

(51) Int. Cl.⁷ ............................................. A47G 29/00
(52) U.S. Cl. .................... 248/689; 248/309.4
(58) Field of Search .................... 248/689, 51, 52, 248/206.5, 309.4; 269/902, 8

(56) References Cited

U.S. PATENT DOCUMENTS

| | | | |
|---|---|---|---|
| 1,984,355 A | * 12/1934 | Abbott | 174/48 |
| 3,324,853 A | * 6/1967 | Czorny et al. | 604/162 |
| 3,514,731 A | * 5/1970 | Drake | 335/285 |
| 4,679,976 A | 7/1987 | Narishige et al. | 414/4 |
| 4,836,244 A | 6/1989 | Ansorge | 137/557 |
| 4,901,446 A | 2/1990 | Narishige | 33/157 |
| 5,227,138 A | * 7/1993 | Boyd et al. | 422/102 |
| 5,456,880 A | 10/1995 | Miura | 422/100 |
| 5,544,747 A | 8/1996 | Horn | 206/378 |
| 5,677,709 A | 10/1997 | Miura et al. | 345/161 |
| 5,853,391 A | * 12/1998 | Bell | 604/160 |

OTHER PUBLICATIONS

Pages from World Wide Web site of Narishige International USA, Inc.

* cited by examiner

*Primary Examiner*—Ramon O. Ramirez
*Assistant Examiner*—Holly N. Sy
(74) *Attorney, Agent, or Firm*—Craig A. Fieschko, Esq.; DeWitt Ross & Stevens S.C.

(57) ABSTRACT

A microtool mount includes an elongated finger terminating in a tip. The finger has a pair of valley edges from which valley walls descend to terminate in a valley floor, thereby defining a valley between the valley walls and floor. The valley extends from the tip along a path parallel to at least a portion of the length of the finger. A microcapillary or other rodlike microtool may be accommodated within the valley, and a fastening member, preferably a magnet, may be removably affixed to the finger above the valley to maintain the microtool within the valley. The valley edges are preferably planar along at least a portion of the length of the finger so as to allow the magnet to more firmly affix to the finger.

20 Claims, 3 Drawing Sheets

MICROTOOL MOUNT

FIELD OF THE INVENTION

This document corcerns as invention relating generally to mounting/gripping apparata for use in the handling and manipulation of microtools (i.e., precision instruments and manipulators for microtechnology and nanotechnology applications, such as fluid-transporting microcapillaries), and more specifically to mounting apparata for quickly and safely receiving and releasing fragile microcapillaries.

BACKGROUND OF THE INVENTION

Capillaries are commonly used in biological applications to sample and transport fluids and/or cells for testing or other purposes. When particularly fine biological microoperations are required—for example, injecting or removing cellular genetic material during in vitro fertilization or cloning operations—microcapillaries are generally used. Microcapillaries are ordinarily prepared by taking a standard glass capillary tube (usually having 1 millimeter diameter), and heating it until it becomes ductile. The capillary is then stretched, causing its diameter to contract. When the capillary is stretched to the desired diameter, generally around 10 microns (inner diameter), it is cooled and allowed to set. The microcapillary's leading edge may then be ground to a point by use of a microgrinder so that it has a sharp leading edge suitable for puncturing a cell membrane.

The microcapillary may then be inserted into the cell, and by decreasing the pressure at the end of the microcapillary, the desired cellular material may be aspirated into the microcapillary. Naturally, such an operation requires very precise control over the positioning of the microcapillary, and therefore mounting/positioning arrangements such as the one shown in FIG. 1 are commonly used. Cellular material is placed on a sampling plate 10 (e.g., a Petri dish or the like). A microscope 12 (or other imaging apparatus) adjacent the sampling plate 10 allows viewing of cells as they are being manipulated. The microcapillary 50 is gripped with a mount 14, with its tip 52 at or slightly above the sampling plate 10. The mount 14 is mounted to an actuator 16, which allows the mount 14 to reposition the microcapillary 50 in at least one dimension in relation to the sampling plate 10 by manipulating a joystick 18 or other input device. A flexible tube 54 fit over the end of the microcapillary 50 leads to a syringe 20 or similar injection device so that suction can be applied to the microcapillary 50. Thus, a user may use the joystick 18 to position the microcapillary 50 as desired, and may use the syringe 20 to withdraw or inject cellular material from or to the cell(s) on the sampling plate 10 when the microcapillary 50 is appropriately positioned.

Problems can occur owing to the attachment between the microcapillary 50 and mount 14, an arrangement which is shown in greater detail in FIG. 2. In general, the mount 14 bears a V-groove 22 wherein the microcapillary 50 may be situated, and a screw-driven clamp 24 is adjusted to bear against the microcapillary 50 and hold it within the groove 22. While this arrangement is simple to manufacture, operate, and maintain, it causes several significant difficulties with use of the microcapillary 50.

First, it is exceedingly easy to either tighten the clamp 24 to such an extent that the microcapillary 50 is crushed, or to conversely leave the clamp 24 so loose that the microcapillary 50 slips within the groove. Breakage is highly inconvenient because the microcapillaries 50 take a long time to prepare, and are usually prepared right before an operation is to be performed to ensure that the microcapillaries 50 are uncontaminated with foreign matter. Since microcapillaries 50 are difficult to properly form and grind and it may take several tries before a suitable microcapillary 50 is obtained, lab personnel generally do not produce a large number of them; therefore, if the available microcapillaries 50 break, lab personnel may be set back by an hour or more as new ones are prepared. This delay may be costly since the cellular material to be operated on may have a limited time window of viability.

Second, the clamp 24 is somewhat time-consuming to deal with. As previously noted, the user must take care when placing a microcapillary 50 in the clamp 24 to be sure that the clamp 24 is neither too loose nor too tight. Further, it is desirable to have a microcapillary 50 which is at least generally well-positioned over the sampling plate 10 prior to the start of the operation: for example, it may be desirable to have it extend from the clamp 24 at or near a certain length, with its sharpened tip 52 being oriented at or near a desired angle. However, to reposition the microcapillary 50 within the clamp 24, the clamp 24 must be unscrewed, the microcapillary 50 must be repositioned, and then the clamp 24 must be carefully screwed down again. These repositioning activities provide further opportunities for lost time and broken microcapillaries 50.

Third, the mount 14 is difficult to use because the user must hold the microcapillary 50 in one hand and simultaneously tighten the clamp 24. Because this is difficult to do with only two hands, the user often initially situates the clamp 24 in an improper position, and must then undergo the aforementioned iterative process of loosening the clamp 24, adjusting the microcapillary 50, and retightening the clamp 24 until the microcapillary 50 is properly positioned.

Since there is an increasing need for speedy and accurate operations on biological materials, particularly where the biological materials have time-limited viability, it would be advantageous to have available a microcapillary mount which overcomes the disadvantages of the prior mounts, and which allows for fast mounting, alignment, and release of microcapillaries, while minimizing the possibility of microcapillary breakage.

SUMMARY OF THE INVENTION

The invention, which is defined by the claims set forth at the end of this document, is directed to mounts for microtools (e.g., microcapillaries) which at least partially alleviate the aforementioned problems. A basic understanding of some of the preferred features of the invention can be attained from a review of the following brief summary of the invention, with more details being provided elsewhere in this document.

To summarize, the microtool mount (as best seen in the different embodiments of FIGS. 3–5) includes an elongated finger terminating in a tip. The finger has a pair of valley edges from which valley walls descend to terminate in a valley floor, thereby defining a valley between the valley walls and floor. The valley extends from the tip along a path parallel to at least a portion of the length of the finger. A microcapillary may be accommodated within the valley (see particularly FIGS. 3 and 4), and a fastening member, preferably a magnet, may be removably affixed to the finger above the valley to maintain the microcapillary within the valley. The valley edges are preferably planar along at least a portion of the length of the finger so as to provide an even surface whereupon the magnet may be more firmly affixed to the finger. The valley is preferably situated within the finger so that a microcapillary resting therein will be aligned with the longitudinal axis of the finger, so that rotation of the finger about this longitudinal axis will also cause the microcapillary to rotate about its longitudinal axis. This allows for greater ease in positioning the microcapillary at desired locations during a biological operation.

In certain preferred embodiments (such as those of FIGS. 4 and 5), at a location spaced rearward of the tip of the finger, one or more of the valley edges has a ledge from which the valley edge begins descending towards the valley floor. A gap is thereby defined in this valley edge and its valley wall. Such a gap may be defined in both valley edges/walls, as illustrated in FIG. 4, or the gap may be defined in one valley edge/wall, as illustrated in FIG. 5. This gap (or gaps) may therefore define a depressed pit spaced rearward from the tip of the finger, behind the mounting surface for the fastening member. The pit provides an enlarged area which better accommodates any flexible lead (e.g., an elastomeric tube, or a flexible wire) trailing from the end of a microtool maintained within the valley, and which allows easier egress of the lead from the finger (see particularly FIG. 4). As illustrated best by the embodiment of FIG. 6 (also shown in FIG. 5), the pit (the element labeled 324 in FIG. 6) may be depressed within the valley so that the length of a microcapillary resting forward of the lead will be cradled within the valley, and the portion of the lead which is fit over the end of the microcapillary will not bias the end of the microcapillary partially out of the valley.

As exemplified by the embodiment of FIG. 5, the valley edges may be formed in two sections, with a distal lower region adjacent to the tip and a proximal raised region spaced from the tip and separated from the lower region by a ledge. A fastening member accommodated on the lower region can therefore be accommodated against the ledge for greater resistance against slipping.

The finger preferably includes a rodlike proximal end opposite the tip, with this proximal end being rotatably journalled within a micromanipulator clip or the like to allow the finger to rotate about the axis of the finger. It is beneficial to situate the valley such that it is coincident with the rotational axis of the finger, so that rotation of the finger about the rotational axis will rotate the microcapillary (or other microtool) about its lengthwise axis as well.

The invention is exceedingly useful for mounting microcapillaries in biological applications such as IVF (in vitro fertilization), particularly ICSI (introcytoplasmic sperm injection); in cloning, where genetic material must be injected or removed; in transgenic technologies; in manipulation of chromosomes; in intracellular electrophysiology; and in so-called "patch clumping" systems. However, the invention may be utilized with numerous microtools apart from microcapillaries, such as microelectrodes, microprobes, nanotips or the like, and may be used in nonbiological operations, e.g., scanning probe microscopy.

Further advantages, features, and objects of the invention will be apparent from the following detailed description of the invention in conjunction with the associated drawings.

DETAILED DESCRIPTION OF PREFERRED EMBODIMENTS OF THE INVENTION

Figure 1:
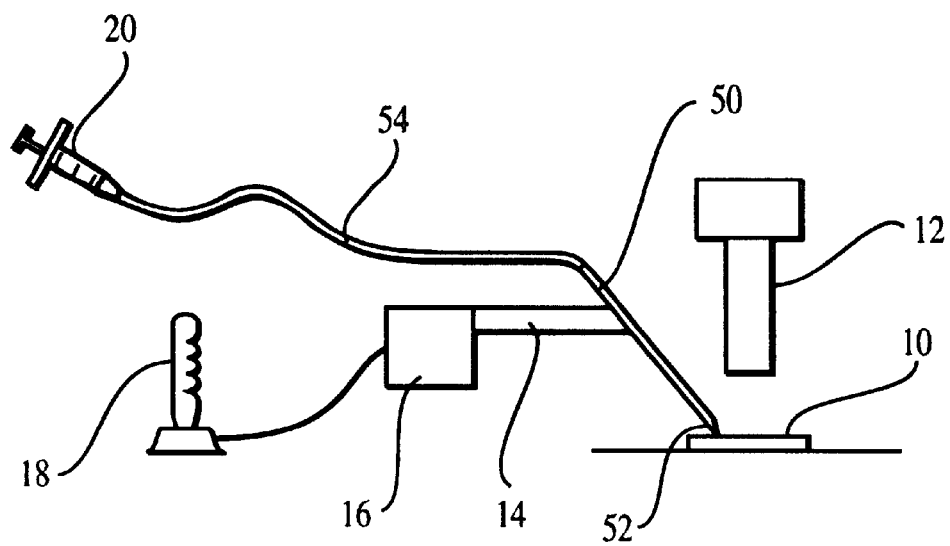
FIG. 1 is a side elevational view of a preexisting microcapillary mounting and positioning arrangement.
Figure 2:
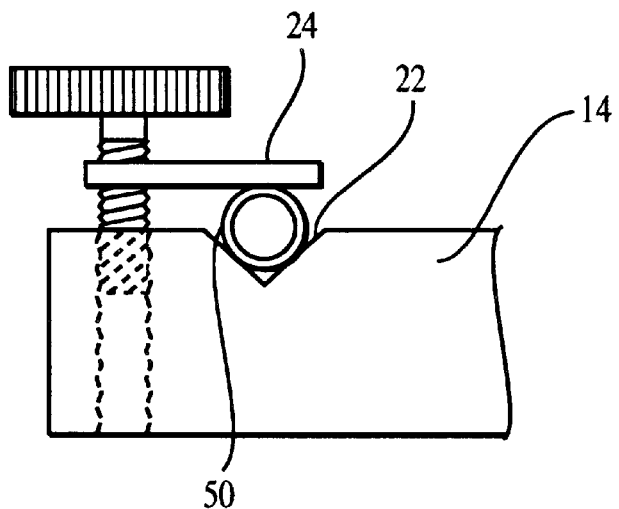
FIG. 2, is a partial bottom elevational view of the mount 14 and microcapillary 50 of FIG. 1.
Figure 3:
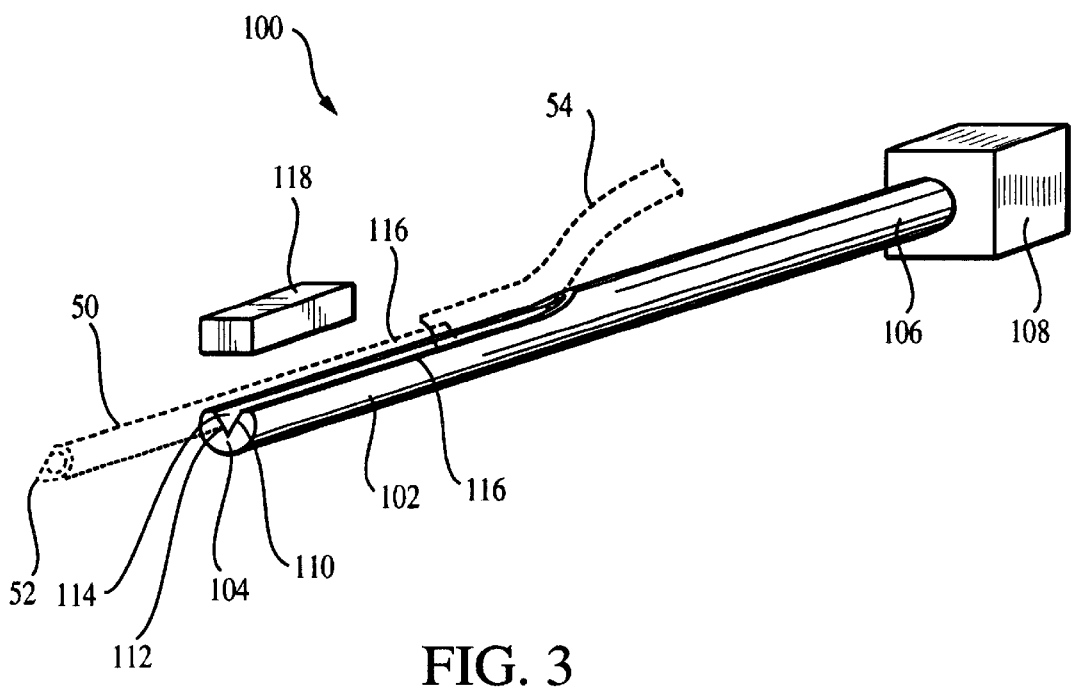
FIG. 3 is a perspective view of a first preferred version of the invention, shown with a capillary 50 (in phantom lines) resting within its finger 102, and with a fastening member 118 detached from and suspended above the finger 102.

Turning initially to FIG. 3, a first preferred version of the microtool mount is designated generally by the reference numeral 100. Since the structure and function of the microtool mount 100 is best understood when described with reference to a particular microtool, the microtool mount 100 will hereinafter be discussed in relation to its use with microcapillaries, and will thus be referred to as the capillary mount 100. However, it is emphasized that the mount 100 is not limited to use with microcapillaries and may be used with other microtools as well.

The capillary mount 100 includes an elongated finger 102 extending between a distal tip 104 and an opposing rod-like proximal end 106. The proximal end 106 can be rotatably journalled within a bearing 108 (which may take a variety of forms, with a simple block-like bearing 108 being illustrated here), or fastened within a micromanipulator, microforge, or the like. The finger 102 has a valley 110 defined along its length, with the valley 110 extending from the tip 104 along a path parallel to the axis of the finger 102. The valley 110 is defined above a valley floor 112 and between a pair of opposing valley walls 114 (only one of these walls 114 being clearly visible in FIG. 3), wherein the valley walls 114 descend from a pair of opposing valley edges 116. In a particularly preferred embodiment of the capillary mount 100, the finger 102 has a diameter of approximately 4 mm, and a valley 110 which measures approximately 3 mm between its valley edges 116; however, it should be understood that the capillary mount 100 may be formed in other sizes.

The valley edges 116 are preferably planar, and resting within a common plane along at least a portion of their length, to allow a level surface for easier and firmer attachment of a fastening member 118. This fastening member 118 may take a variety of forms, but it is preferably provided in the form of a magnet (and most particularly a rare earth magnet) which is capable of removable affixment to the finger 102 above the valley 110 by contacting one or both of the valley edges 116. Naturally, if the fastening member 118 is magnetic, at least a portion of the finger 102 must be made of a material which is capable of being magnetically attracted, such as steel or another ferromagnetic material. Most preferably, the finger 102 is made of ferromagnetic stainless steel to allow its sterilization, and the fastening member 118 is a rare earth magnet which does not lose its magnetic properties at the sterilization temperature.

Using the capillary mount 100, a capillary 50 (shown in phantom lines), with a trailing lead 54 (e.g., a flexible tube, also shown in phantom lines) may be situated within the valley 110 with the tip 52 of the capillary 50 extending forward from the tip 104 of the finger 102, and with the lead 54 extending out of the valley 110 near the end of the finger 102 to a syringe or similar injection/suction apparatus. The fastening member 118 may be situated atop the capillary in contact with one or both of the valley edges 116, with the magnetic attraction between the fastening member 118 and the finger 102 firmly maintaining the capillary 50 within the valley 110 (even when the fastening member 118 only contacts one of the valley edges 116). The fastening member 118 is very quickly and easily attached and detached from the finger 102 to allow insertion and removal of the capillary 50, while at the same time is does not exert such force on the capillary 50 that it is likely to be crushed between the fastening member 118 and the finger 102 owing to the limited magnetic forces between them.

It is particularly preferred that the valley 110 be defined within the finger 102 in such a manner that capillary 50 doesn't lie upon or touch the valley floor 112, so that it may not roll about the valley floor 112 in directions perpendicular to the axis of the valley 110. Thus, a V-shaped valley 110, which only provides two points of contact between the capillary 50 and the valley 110, is preferred. It is also particularly preferred that the valley 110 be defined within the finger 102 at such a depth and position that the longitudinal axis of a capillary 50 situated within the valley 110 will be aligned at least substantially coincident with the rotational axis of the finger 102. As a result, when the finger 102 is rotated about its rotational axis within the bearing 108, the capillary 50 will rotate about its axis with little or no eccentricity. This allows rotation of the finger 102 so that the tip 52 of the capillary 50 may be precisely oriented as desired, and also allows the tip 52 to be moved in a drill-like fashion.

The ability of the fastening member 118 to fix the capillary 50 within the valley 110 of the finger 102 may be enhanced if the fastening member 118 is given a soft, compressible, non-abrasive cover, such as a rubber coating, so that the cover can compress where it is in contact with the capillary 50 to complementarily fit about a portion of its circumference. Teflon is a particularly preferred coating because it is inert and resists corrosion. For an easy and low-cost alternative to a rubber or Teflon coating, it has been found that the fastening member 118 functions quite well when it is simply provided with glued-on paper or cardboard on the face which contacts the finger 102 and capillary 50.

It is noted that because the valley 110 does not extend along the entire length of the finger 102, and terminates at a location spaced from the tip 104, the capillary 50 is deterred from sliding axially rearward within the valley 110 because the capillary 50 (or the lead 54 attached to its end) will interfere with the end of the valley 110. Additionally, the trailing lead/tube 54 of the capillary 50 is generally made of flexible rubber, which tends to prevent the capillary 50 from sliding within the valley 110 owing to the frictional properties of the lead 54. This is in contrast to prior capillary mounts wherein only the glass portion of the capillary 50 is grasped by a clamp, thereby increasing the possibility of the capillary 50 sliding within the clamp owing to the low friction of the glass.

Figure 4:
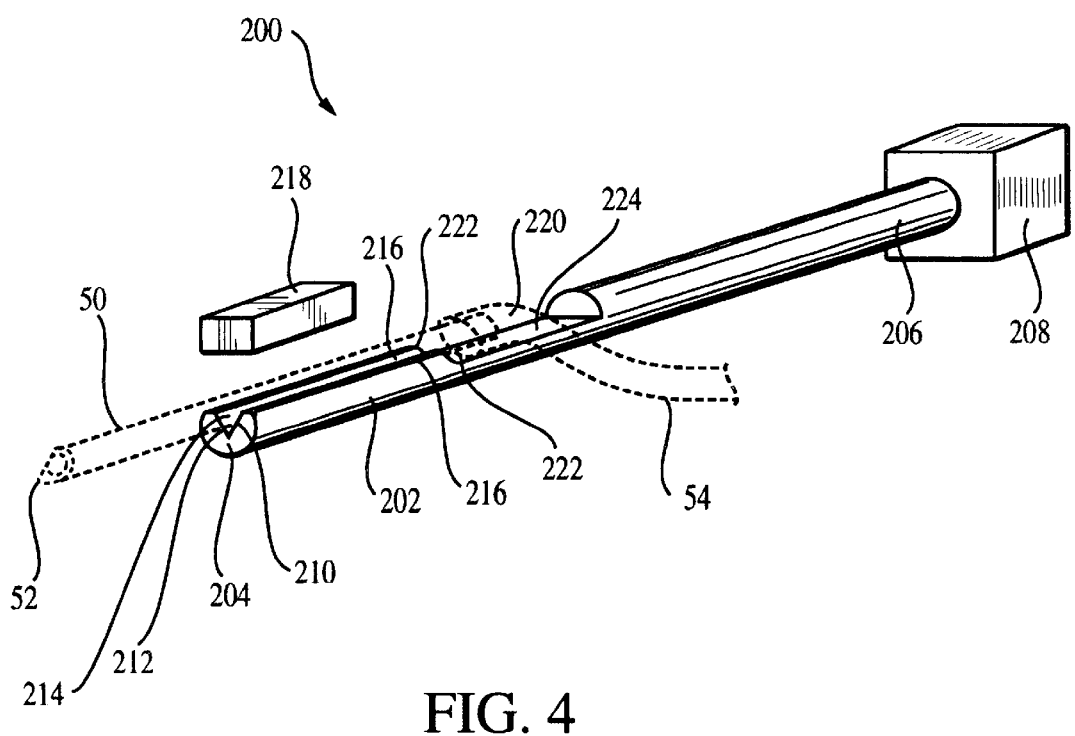
FIG. 4 is a perspective view of a second preferred version of the invention, shown with a capillary 50 (in phantom lines) resting within its finger 202, and with a fastening member 218 detached from and suspended above the finger 202.

In FIG. 4, a second version of the capillary mount is designated generally by the reference numeral 200. The capillary mount 200 has a number of features similar to those of the capillary mount 100, and includes an elongated finger 202 extending between a distal tip 204 and an opposing rod-like proximal end 206. The proximal end 206 is shown rotatably journalled within a simple bearing 208 of a micromanipulator (though it may be otherwise affixed to a micromanipulator). A valley 210 extends from the tip 204 along a portion of the length of the finger 202, and is defined above a valley floor 212 and between a pair of opposing valley walls 214 (only one of these walls 214 being clearly visible in FIG. 4). These valley walls 214 descend from a pair of opposing valley edges 216, which are preferably at least substantially planar and situated within a common plane to more easily accommodate attachment of a fastening member 218. The valley walls 214 each have a gap 220 defined therein at a location spaced from the tip 204 (preferably at the end of the valley 210). Thus, the valley edges 216 descend downwardly towards the valley floor 212 at a location spaced from the tip 204, so that each of the valley walls 214 and edges 216 extends between the tip 204 and a proximal ledge 222. As a result of the lack of valley walls 214 at the gap 220, an open area level with the valley floor 212 is provided; this open area will be referred to herein as the pit 224. The valley 210 therefore extends rearward from the tip 204 of the finger 202 to open upon the pit 224, and as a result, a capillary 50 with a trailing lead 54 (i.e., an elastomeric tube) may be fit within the valley 210 so that its lead 54 can extend outwardly from the finger 202 at the pit 224. Because the lead 54 of the capillary 50 cannot easily slide forward of the ledges 222 if the valley 210 is sized to closely receive the capillary 50, and because the capillary 50 cannot slide within the valley rearward of the pit 224, this capillary mount 200 very firmly maintains the capillary 50 against axial sliding.

Figure 5:
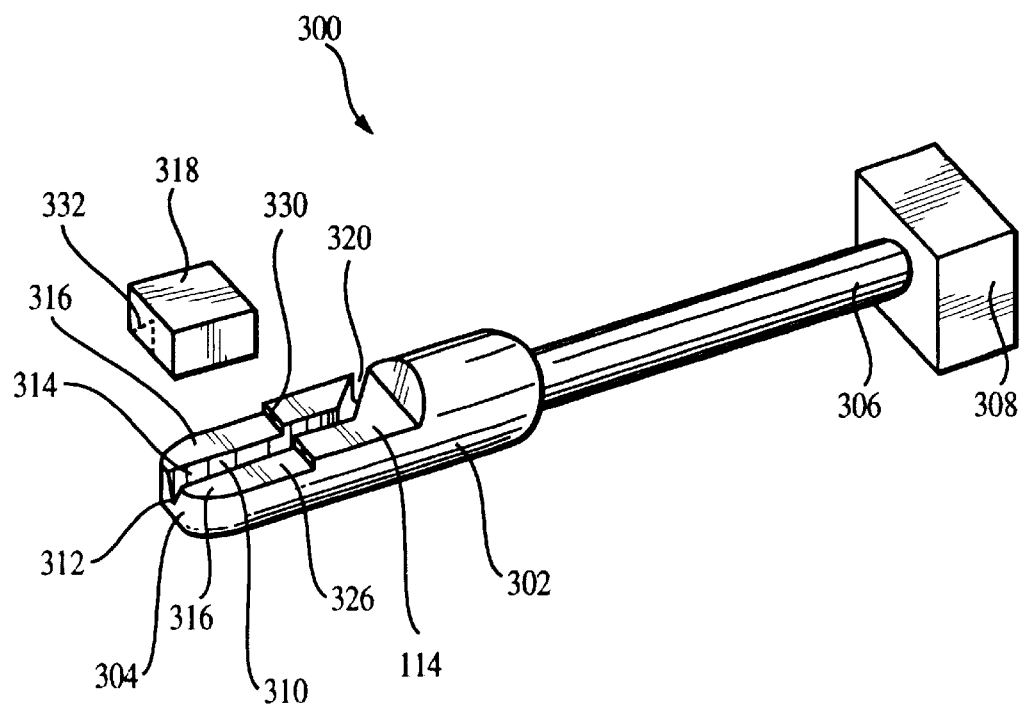
FIG. 5 is a perspective view of a third preferred version of the invention, shown with a fastening member 318 detached from and suspended above the finger 302.
Figure 6:
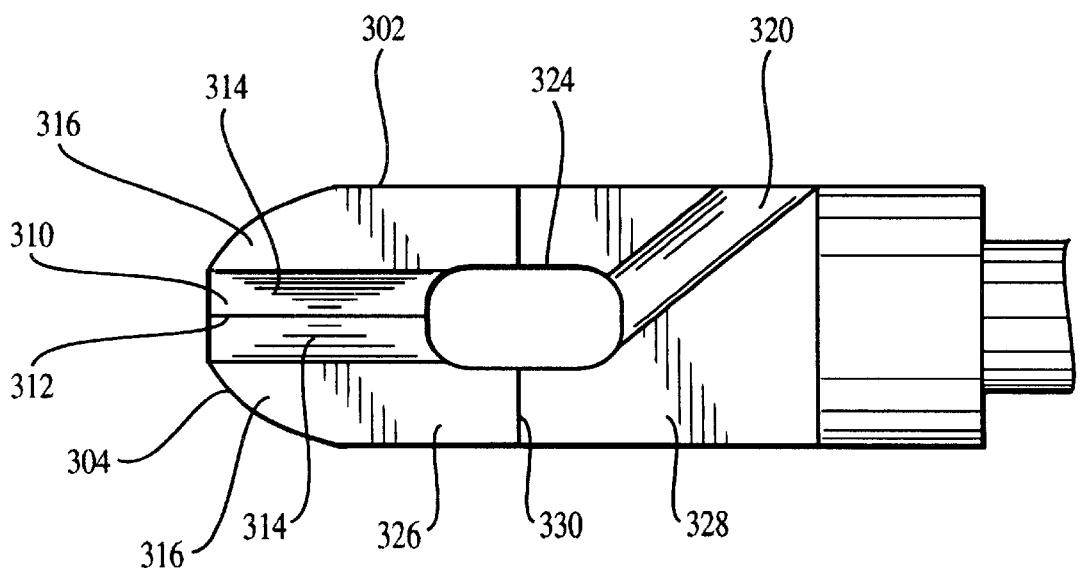
FIG. 6 is a partial top elevational view of the finger 302 of FIG. 5.

A third and particularly preferred version of the capillary mount is then illustrated in FIGS. 5 and 6, with the overall capillary mount being designated by the reference numeral 300. The capillary mount 300 includes an elongated finger 302 extending between a distal tip 304 (shown in greater detail in FIG. 6) and an opposing rod-like proximal end 306, with the proximal end 306 being rotatably mounted within a bearing 308 of a micromanipulator (though other attachments to micromanipulators are possible). The finger 302 includes two opposing valley edges 316 which have descending valley walls 314 joining a valley floor 312, and thereby defining a valley 310 which extends along a path parallel to a portion of the length of the finger 302. At a location spaced rearward from the tip 304, the valley 310 descends into a depressed pit 324 (visible only in the top view of FIG. 6). The valley 310 then preferably ascends to a level at or near its height near the tip 304, and proceeding further rearward, it bends laterally to define a gap 320 in one of the valley walls 314. As can be seen particularly well in FIG. 5, the valley edges 316 are formed in two sections: a distal lower region 326 adjacent to the tip 304, and a proximal raised region 328 spaced from the tip 304. The valley edges 316 at both the lower region 326 and raised region 328 are both substantially planar. The aforementioned pit 324 is preferably provided in the valley 310 in such a location that it extends adjacent to a portion of both the lower region 326 and the raised region 328. In a particularly preferred embodiment of the capillary mount 300, the finger 302 has a lateral width of approximately 1 cm at its widest point; the valley edges 316 each have a lateral width of approximately 4 mm at their widest points; the valley 310 has a lateral width of approximately 2 mm between the valley edges 316, a depth of approximately 11.5 mm, and a length of approximately 1 cm between the tip 304 and the pit 324; the pit 324 has a lateral width of approximately 3 mm, a depth of approximately 2–2.5 mm, and a length of approximately 5 mm; and the valley 310 extends approximately 5 mm rearward from the pit 324 before curving laterally to open at the gap 320, and has a lateral width of approximately 3 mm over this portion. The distal lower region 326 and proximal raised region 328 have a height difference of approximately 0.5 mm. A fastening member 318 which is removably affixable to the finger 302 is again provided, with the fastening member 318 preferably being provided in the form of a magnet.

In operation, the capillary mount 300 receives a capillary tube within its valley 310, and the fastening member 318 is then affixed atop the lower region 326 of the valley edges 316 to hold the capillary tube within the valley 310. The adherence of the fastening member 318 to the finger 302 is somewhat increased by the ledge 330 defined between the lower and raised regions 326 and 328 of the valley edges 316. At the area where a tube is fit over the end of the capillary (thereby providing the end of the capillary with an area of increased diameter) or a different lead is otherwise affixed to the capillary, the pit 324 is provided to accommodate this enlarged diameter so that the remainder of the capillary 50 will not be biased upward, and will still rest against the valley walls 314. Additionally, the pit 324 allows for greater flexibility of the trailing lead with respect to the capillary so that if the lead exits the finger 302 at the pit 324, the lead is not so rigidly tethered to the capillary that tension on the lead will transfer directly to the capillary, increasing its likelihood of being dislodged within the valley 310. If the gap 320 is provided, the trailing lead of the capillary can extend out of the pit 324 and through the gap 320 to trail rearward to a syringe or other apparatus. As in the capillary mounts 100 and 200, the valley 310 of the capillary mount 300 is preferably aligned such that a capillary resting therein will be coaxial with (or close to coaxial with) the rotational axis of the finger 302 within the bearing 308.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. Following is an exemplary list of such modifications.

First, it is also possible for the fastening member to have a valley defined therein in addition to (or in lien of) the valley defined in the finger, with an exemplary fastening member valley 332 being illustrated in phantom lines in FIG. 5. If the fastening member valley 332 is provided in lieu of the valley 310 in the finger 302, the fastening remember valley 332 can work in combination with the pit 324, and with the gap 320 in the valley wall 314, to allow a capillary to fit within the fastening member valley 3321 the capillary end and surrounding lead to be fit within the pit 324; and the trailing lead to extend out of the pit 324 and gap 320. Advantageously, the fastening member 318 may bear the fastening member valley 332 on one of its faces for optional use, and its opposite face need not include a fastening member valley. This allows the face bearing the valley 332 to be affixed to the valley edges 316 when a fastening member valley 332 is useful in conjunction with a valley 310, and otherwise the opposite face of the fastening member 318 may be adhered to the valley edges 316 when no valley 332 is needed. Another alternative is to provide a number of differently-sized valleys on different faces of the fastening member 318 so that the valley having the desired size may be chosen by simply affixing the corresponding side of the fastening member 318 to the finger 302. It should be understood that when a fastening member valley 332 is used in combination with the valley 310 in the finger 302, this allows capillaries of greater diameter to be accommodated.

Second, it is noted that while a V-groove is shown throughout the Figures as forming the valleys of the various capillary mounts 100, 200, and 300, valleys having other configurations may be used, e.g., rectangular grooves, trapezoidal grooves, or grooves of other shapes. However, as previously noted, it is preferable to choose a valley configuration which resists rolling of the capillary within the valley. Naturally, the valleys must be sized and configured in relation to the capillaries to be held within the valleys so that the capillaries will partially protrude out of the tops of the valleys, so that the fastening members may bear against them to maintain them within the valleys. For example, the depth of the valley 110 between the valley edges 116 and the valley floor 112, and the angles between the valley walls 114 and the valley floor 112, must be sized so that a capillary within the valley 110 will protrude at least slightly above the valley edges 116, so that the fastening member 118 will bear against it and hold it in the valley 110.

Third, while a magnetic fastening member is particularly preferred owing to its ease of attachment and detachment to a ferromagnetic finger, and its decreased tendency to break the capillary, other forms of fastening members may be used instead. Alternative fastening members could include rubber bands, wire twists, tape, clips, and the like, all of which may be fit about the capillary and all or a portion of the circumference of the finger. The fastening member and finger may have cooperating and/or complementary connecting structures, such as male members on the fastening member which are received within female apertures in the finger, to achieve the attachment function. Adhesives such as rubber cement, paraffin, and household glue may also be used to maintain the capillary within the valley of the finger (or fastening member); if the finger is relatively smooth, such adhesives will adhere the capillary within the valley, but can be easily peeled away when the capillary is removed. The fingers previously shown and illustrated therefore have utility even when no or different fastening members are used.

Fourth, it is similarly noted that fastening members bearing valleys, such as the fastening member 318 and its valley 332, similarly have utility if used without a finger because they may be used to hold microcapillaries or other microtools against ferromagnetic structures, e.g., against parts of a microscope, microgrinder, microforge, etc. The microtool may be inserted within the valley, and the fastening member can then be magnetically adhered to the desired structure with the microtool maintained in the valley between the fastening member and the structure, to hold the microtool in a desired position and orientation. As an example, it is often convenient to affix pre-prepared microcapillaries to a microscope to keep them in a safe place where they are readily available for usage. It is also possible to use a pair of fastening members to mount microcapillaries or other microtools to laboratory structures by "sandwiching" the microtool between the fastening members, and then adhering the fastening members to desired laboratory structures. In this arrangement, one or both of the fastening members may include valleys; additionally, only one or both of the fastening members need be magnetic. It is preferable that both be magnetic, since each may then be used to grip microtools against a metallic mounting structure, or alternatively each may be used with the other fastening member to grip microtools away and apart from any other metallic mounting structure.

Fifth, it should be understood that the mounts illustrated and described herein may be suitable for use with microtools other than microcapillaries, such as fiberoptic probes, heating filaments, and other elongated probing, sampling, testing, and operating devices. Additionally, the mounts are not limited to use in biological operations, and may be used in microelectronics applications, scanning probe microscopy, and other operations.

Sixth, it should be understood that just as the fastening members may contain more than one valley, so may the various fingers of the mounts. For example, a mount may contain multiple valleys defined in its finger, either oriented side-by-side in a parallel array or on different sides of the finger at different orientations. A user may therefore use only one of the valleys, or may utilize several of them at the same time if several microtools are needed.

Seventh, while the invention is generally described as using a ferromagnetic finger and a magnetic fastening member, it should be understood that it is also possible to use a magnetic finger and a ferromagnetic fastening member.

It should be understood that preferred versions of the invention have been described above in order to illustrate how to make and use the invention. The invention is not intended to be limited to these embodiments, but rather is intended to be limited only by the claims set out below. Thus, the invention encompasses all alternate embodiments that fall literally or equivalently within the scope of these claims.

What is claimed is:

1. A mount for microtools comprising:
   a. an elongated finger terminating in a tip, the finger having a valley defined therein, the valley including a pair of opposing valley walls descending between two valley edges to a valley floor, wherein the valley extends from the tip along a path parallel to at least a portion of the length of the finger;
   b. a magnetic fastening member removably affixable to the finger above the valley,
   whereby an elongated microtool may be mounted lengthwise within the valley between the valley floor and the fastening member.

2. The mount of claim 1 wherein the valley edges are planar along at least a portion of the length of the finger.

3. The mount of claim 1 wherein the finger includes a proximal end opposite the tip, and wherein the proximal end is rotatably journalled within a bearing whereby the finger is rotatable about a rotational axis.

4. The mount of claim 3 wherein the rotational axis is coincident with the valley.

5. The mount of claim 1 wherein the fastening member includes a valley defined therein.

6. The mount of claim 1 wherein the valley edges descend downwardly towards the valley floor starting at a ledge spaced from the tip.

7. The mount of claim 1 wherein at least one of the valley walls has a gap therein, the gap being defined at a location spaced from the tip.

8. The mount of claim 1 wherein the valley includes a pit depressed therein, the pit being spaced from the tip.

9. The mount of claim 1 wherein the valley is at least substantially linear adjacent the tip, and wherein the valley bends at a location spaced away from the tip.

10. The mount of claim 1 wherein the valley edges include a distal lower region adjacent to the tip, and a proximal raised region spaced from the tip.

11. The mount of claim 10 wherein at least one of the valley walls has a gap therein, the gap being defined through the proximal raised region.

12. A mount for microtools comprising:
    a. a finger terminating in a tip, the finger including a pit depressed therein, the pit being spaced from the tip,
    b. a magnetic fastening member removably affixed to the finger,
       wherein at least one of the finger and the fastening member bears a valley defined therein, the valley extending from the tip between the finger and the fastening member to open upon the pit,
       whereby an elongated microtool having a distal end with a flexible lead extending therefrom may be accommodated within the mount with the microtool situated within the valley and its distal end situated within the pit.

13. The mount of claim 12 wherein the fastening member includes a valley defined therein.

14. The mount of claim 12 wherein the valley is defined in the finger, and extends from the tip to the pit.

15. The mount of claim 14 wherein:
    the finger includes a pair of opposing valley edges extending from the tip;
    the valley edges having valley walls descending therefrom to define the valley therebetween;
    the valley edges being at least substantially planar.

16. The mount of claim 14 wherein:
    the finger includes a pair of opposing valley edges extending from the tip, the valley edges including:
    a. valley walls descending therefrom to define the valley therebetween;
    b. a distal depressed region adjacent to the tip, and
    c. a proximal raised region spaced from the tip.

17. The mount of claim 14 wherein:
    the finger includes a pair of opposing valley edges extending from the tip;
    the valley edges having valley walls descending therefrom to define the valley therebetween;
    at least one of the valley walls including a gap therein, the gap being spaced from the tip.

18. A mount for microtools comprising a finger terminating in a tip, the finger including:
    a. a pair of closing valley edges extending from the tip, the valley edges having valley walls descending therefrom to define a valley extending from the tip,
       wherein at least one of the valley walls includes a gap therein, the gap being spaced from the tip.
    b. a pit depressed within the valley, the pit being spaced from the tip, whereby an elongated microtool having a distal end with a flexible lead extending therefrom may be accommodated upon the finger with the microtool situated within the valley, its distal end situated within the pit, and its lead extending through the gap.

19. The mount of claim 18 further comprising a magnetic fastening member removably affixed to the finger above the valley.

20. The mount of claim 19 wherein the fastening member includes a valley defined therein.

* * * * *